(12) United States Patent
Sacchetti et al.

(10) Patent No.: US 10,406,076 B2
(45) Date of Patent: *Sep. 10, 2019

(54) ENTERAL FEEDING PUMP SYSTEM

(71) Applicant: Alcor Scientific, Inc., Smithfield, RI (US)

(72) Inventors: Peter J. Sacchetti, Attleboro, MA (US); Ralph Beckman, Providence, RI (US)

(73) Assignee: Alcor Scientific, Inc., Smithfield, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/882,606

(22) Filed: Jan. 29, 2018

(65) Prior Publication Data

US 2018/0147123 A1 May 31, 2018

Related U.S. Application Data

(60) Continuation-in-part of application No. 14/979,267, filed on Dec. 22, 2015, now Pat. No. 9,993,392, (Continued)

(51) Int. Cl.
| | |
|---|---|
| *A61J 15/00* | (2006.01) |
| *A61M 5/142* | (2006.01) |
| *B65H 75/28* | (2006.01) |
| *A61M 5/168* | (2006.01) |
| *B65H 54/04* | (2006.01) |
| *A61M 39/08* | (2006.01) |

(Continued)

(52) U.S. Cl.
CPC ....... *A61J 15/0076* (2015.05); *A61J 15/0011* (2013.01); *A61J 15/0092* (2013.01); *A61M 5/14212* (2013.01); *A61M 5/14228* (2013.01); *A61M 5/16881* (2013.01); *A61M 39/08* (2013.01); *B65H 54/04* (2013.01); *B65H 75/28* (2013.01); *F04B 43/08* (2013.01); *F04B 43/12* (2013.01); *A61J 9/005* (2013.01); *A61M 2202/0482* (2013.01); *B65H 2701/33* (2013.01)

(58) Field of Classification Search
CPC .......... A61J 15/0011; A61J 15/0076; A61J 15/0092; A61J 9/005; A61M 2202/0482; A61M 39/08; A61M 5/14212; A61M 5/14228; A61M 5/16881; B65H 2701/33; B65H 54/04; B65H 75/28; F04B 43/08; F04B 43/12

See application file for complete search history.

(56) References Cited

U.S. PATENT DOCUMENTS

| | | | |
|---|---|---|---|
| 1,856,350 A | 5/1932 | Metcalf | |
| 2,318,721 A | 5/1943 | Siver | |

(Continued)

OTHER PUBLICATIONS

International Search Report and Written opinion received in International Application No. PCT/US2009/048053, dated Aug. 19, 2009, 9 pages.

*Primary Examiner* — Brandy S Lee
(74) *Attorney, Agent, or Firm* — Adler Pollock & Sheehan P.C; Daniel J Holmander Esq.

(57) ABSTRACT

Methods and apparatus for an enteral feeding pump system. A method of directing flow for a coil includes drawing fluid from a source and delivering fluid, the coil including input and output check valves to prevent a back flow of fluid.

4 Claims, 8 Drawing Sheets

Related U.S. Application Data which is a division of application No. 13/731,048, filed on Dec. 30, 2012, now Pat. No. 9,233,053, which is a continuation-in-part of application No. 12/488,460, filed on Jun. 19, 2009, now Pat. No. 8,449,501.

(60) Provisional application No. 61/073,964, filed on Jun. 19, 2008.

(51) Int. Cl.
  *F04B 43/08* (2006.01)
  *F04B 43/12* (2006.01)
  *A61J 9/00* (2006.01)

(56) References Cited

U.S. PATENT DOCUMENTS

| | | | |
|---|---|---|---|
| 2,343,727 A * | 3/1944 | Zenner | F17C 9/02 |
| | | | 165/145 |
| 2,377,170 A | 5/1945 | Morgan | |
| 2,387,215 A | 10/1945 | Fawkes | |
| 2,602,764 A | 7/1952 | Billingham | |
| 3,482,660 A | 12/1969 | Garnett | |
| 3,554,224 A | 1/1971 | Kirk et al. | |
| 3,685,532 A | 8/1972 | Kasschau | |
| 3,720,221 A | 3/1973 | Hufeld et al. | |
| 3,853,145 A | 12/1974 | Judd | |
| 4,016,897 A | 4/1977 | Asioli | |
| 4,116,216 A | 9/1978 | Rosenberg | |
| 4,155,362 A | 5/1979 | Jess | |
| 4,173,233 A | 11/1979 | Snyder | |
| 4,178,963 A | 12/1979 | Riefler et al. | |
| 4,221,238 A | 9/1980 | Madsen | |
| 4,276,333 A | 6/1981 | Cobean | |
| D287,044 S | 12/1986 | Hughes | |
| 4,632,361 A | 12/1986 | Callison | |
| 4,657,490 A | 4/1987 | Abbott | |
| 4,673,397 A | 6/1987 | Lynn et al. | |
| 4,710,166 A | 12/1987 | Thompson et al. | |
| 4,718,896 A | 1/1988 | Amdt et al. | |
| 4,729,406 A | 3/1988 | Frentzel | |
| 4,820,265 A | 4/1989 | DeSatnick et al. | |
| 4,845,487 A | 7/1989 | Frantz et al. | |
| 5,022,426 A | 6/1991 | Fischer | |
| 5,209,654 A | 5/1993 | Lofsjogard Nilsson et al. | |
| 5,408,990 A | 4/1995 | Edling et al. | |
| 5,458,578 A | 10/1995 | Sebesta et al. | |
| 5,514,102 A | 5/1996 | Winterer et al. | |
| 5,810,323 A | 9/1998 | Winterer et al. | |
| 5,810,770 A | 9/1998 | Chin et al. | |
| 5,958,167 A | 9/1999 | Van Driel et al. | |
| 5,964,580 A | 10/1999 | Taga | |
| 6,039,078 A | 3/2000 | Tamari | |
| 6,128,884 A | 10/2000 | Berdan, II et al. | |
| 6,371,732 B1 | 4/2002 | Moubayed et al. | |
| 6,607,368 B1 | 8/2003 | Ross et al. | |
| 6,622,933 B1 | 9/2003 | Young et al. | |
| 6,626,329 B2 | 9/2003 | Rake et al. | |
| 8,137,083 B2 | 3/2012 | Zhou | |
| 8,137,541 B2 | 3/2012 | Zook | |
| D667,350 S | 9/2012 | Smith | |
| 8,771,228 B2 | 7/2014 | Butterfield | |
| 8,986,252 B2 | 3/2015 | Cummings et al. | |
| 9,233,053 B2 | 1/2016 | Sacchetti et al. | |
| 9,468,715 B2 | 10/2016 | Tsoukalis | |
| 9,993,392 B2 | 6/2018 | Sacchetti et al. | |
| 2001/0044603 A1 | 11/2001 | Harrold | |
| 2004/0026525 A1 | 2/2004 | Fiedrich | |
| 2004/0108333 A1 | 6/2004 | Rake et al. | |
| 2005/0209563 A1 | 9/2005 | Hopping et al. | |
| 2007/0107364 A1 | 5/2007 | Estes et al. | |
| 2008/0051697 A1 * | 2/2008 | Mounce | A61M 5/1413 |
| | | | 604/32 |
| 2009/0019802 A1 | 1/2009 | Crall, Jr. | |
| 2009/0159577 A1 | 6/2009 | Sommerfeld | |
| 2009/0199915 A1 | 8/2009 | Novacek et al. | |
| 2009/0229692 A1 | 9/2009 | Rohwer et al. | |
| 2010/0168652 A1 | 7/2010 | Landherr et al. | |
| 2012/0096785 A1 | 4/2012 | Weeks | |
| 2015/0139836 A1 | 5/2015 | Norman et al. | |
| 2016/0067148 A1 | 3/2016 | Nordquist et al. | |
| 2017/0128652 A1 | 5/2017 | McGill et al. | |

* cited by examiner

ENTERAL FEEDING PUMP SYSTEM

CROSS REFERENCE TO RELATED APPLICATIONS

This application is a continuation-in-part of non-provisional patent application Ser. No. 14/979,267 filed Dec. 22, 2015, which is related to non-provisional application Ser. No. 13/731,048 filed Dec. 30, 2012, now U.S. Pat. No. 9,233,053, and claims priority from non-provisional patent application Ser. No. 12/488,460 filed Jun. 19, 2009 and earlier filed provisional patent application Ser. No. 61/073,964 filed Jun. 19, 2008. The disclosures of all of these applications are incorporated by reference in their entirety for all purposes.

BACKGROUND OF THE INVENTION

The invention generally relates to enteral feeding systems, and in particular, to an enteral feeding pump system.

In general, a fluid pump has a mechanism which imparts force on fluid contained within an enclosed volume. This enclosed volume has output and input tubes through which the forced fluid is expelled and replaced. In the case of enteral feeding, liquid nutrient is accurately delivered into the patient gastrointestinal tract at a controlled rate. Standard versions of enteral feeding pump systems utilize disposable tubing sets which include a peristaltic pumping section. This peristaltic section is installed in tension against a rotor, which moves fluid from a source, through the pump and into the patient. Tubing sets of this design are relatively higher cost than ones manufactured to the design specified in, for example, U.S. Pat. No. 8,449,501, assigned to Alcor Scientific Inc.

A pumping system using pumping sets with a pre-formed coil configuration according to the original invention installed as an accessory to a pump with linear actuator mechanism and output and input pinch valves has been demonstrated to have equivalent performance at reduced cost. The pre-formed coil is symmetrical along the central diametric axis. In its simplest embodiment, it is possible for a pump user to install the pre-formed tubing in either of two orientations. One case will allow fluid to flow correctly from the source container to the patient connection. The other would result in incorrect reverse fluid flow from patient to source container.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention provides methods and apparatus for an enteral feeding pump system.

In one aspect, the invention features a method of directing flow for a coil that draws fluid from a source and delivers fluid, the coil including input and output check valves to prevent a back flow of fluid.

In another aspect, the invention features a method for flowing fluid including providing a fluid delivery set having a source end and a patient end with a repeatable compression portion intermediate the ends, the fluid delivery set comprising a disposable tubing set made of low-grade PVC tubing throughout its length, providing an enteral feeding pump for regulating the flow of fluid into and out of the fluid delivery set, compressing said repeatable compression portion made of low-grade PVC tubing of said fluid delivery set using the enteral feeding pump, selectively closing a first means for regulating the flow of medical fluid out of the compression portion, and selectively opening a second means upstream of the repeatable compression portion for regulating the flow of medical fluid into the compression portion from the source end, the first means and the second means comprising check valves positioned at opposite ends of the disposable tubing set.

In still another aspect, the invention features a disposable fluid delivery set assembly including a source end, a compression portion, and a patient end connector with an integral check valve, the integral check valve having a cracking pressure that is higher than a maximum elevation difference between a source container and a patient, preventing excess flow and enabling unidirectional pumping when a proximal tubing section relative to the compression portion is captured in a pinch valve.

In another aspect, the invention features a method for flowing fluid unidirectionally using an enteral pumping system including a disposable fluid delivery set and enteral feeding pump for delivery medical fluids including providing a fluid delivery set which includes a source end, a patient end, and the repeatable compression portion, providing the enteral feeding pump is for repeatable compressing of the compression portion and regulating the flow of fluid into and out of the compression portion, inserting the fluid delivery set into the enteral feeding pump, compressing the repeatable compression portion of the fluid delivery set using the enteral feeding pump, closing the flow of medical fluid out of the compression portion with a regulating means and into the patient end using the enteral feeding pump, opening the regulating means opens to cause the flow of medical fluid into the compression portion from the source end using the enteral feeding pump, releasing the compressed portion using the enteral feeding pump to allow medical fluids to be drawn into the fluid delivery set through the regulating means and into the compression portion from the source end, closing the regulating means to close the flow of medical fluid into the compression portion from the source end using the enteral feeding pump, and compressing the compressing portion by the enteral feeding pump to move medical fluids out of the compression portion, through the regulating means, and into the patient end.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The invention will be more fully understood by reference to the detailed description, in conjunction with the following figures, wherein.

DETAILED DESCRIPTION

Figure 1:
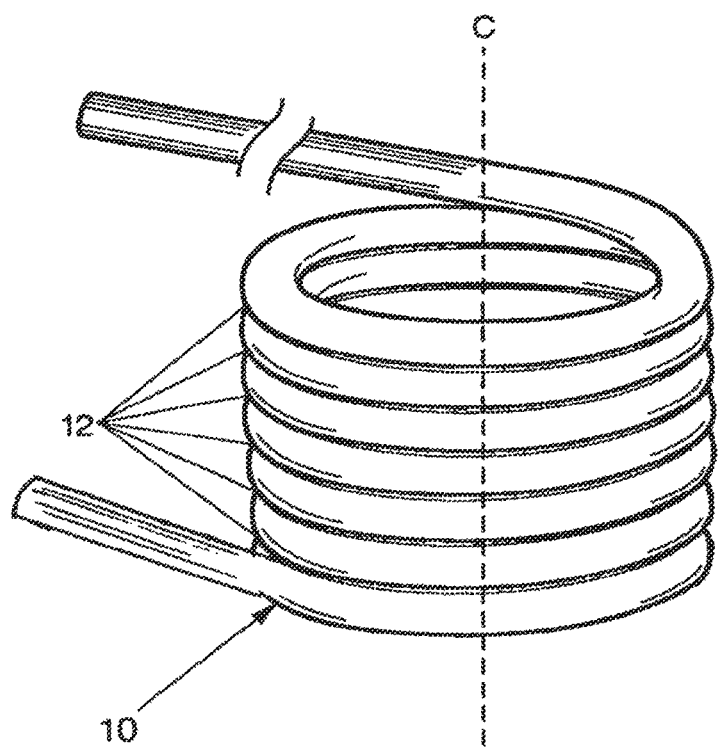
FIG. 1 is a perspective view of a compression portion of a disposable fluid delivery set; (10) is the coil formed with bonded adjacent turns. (12) extended tubing ends. (10b & 10c) serve as either input or output ports.

The invention described herein features a method of directing flow for a coil tubing set that draws fluid from a source and delivers fluid to a patient using a pump with flow-directing pinch valves. The pump is designed to receive and retain a coil between two opposing platens. One or both may be cyclically translated to cause axial compression. The compression force is measured by an integral force sensor mounted in one of the pump platens. The compression and release of the coil causes fluid to enter and exit the enclosed volume. In order to obtain unidirectional flow, tubing extending out from each end of the coil is introduced into a pinch valve. When the pump is activated, the two pinch valves, depending on their sequencing, open and close to cause fluid to flow in either direction. A controller sets the valve operation sequence.

The symmetrical coil set can be installed in the pump in either of two orientations. When pumping is started, a process of pumping and force sensing is applied to select the proper flow direction. The proper flow direction, from source container to patient, is decided by indirect measurement of pressure on the force sensor. If the default flow direction is from the patient end to the source container, the pressure is higher than if the direction is from the source container to the patient end of the tubing. This pressure difference allows determination of the formula flow direction. The controller sets the preferred direction for the immediately installed coil set. A new flow direction is determined for subsequently installed coil sets.

The invention generally relates to enteral feeding systems, and in particular enteral feeding pump systems. More specifically, the invention relates to an enteral feeding pump system for delivering medical fluids unidirectionally including a disposable fluid delivery set having a repeatable compression portion which is helically coiled to define a cylindrical shape. The compression portion pumps a large volume of medical fluids per stroke. Also, an enteral feeding pump configured to repeatedly and reliably compress the compression portion of the fluid delivery set along a central axis.

Referring to FIGS. 1-7, an enteral pump feeding system 60, 70 for delivering medical fluids unidirectionally includes a disposable or replaceable fluid delivery set 20, 30 having a repeatable compression portion 10 and an enteral feeding pump 40. The disposable fluid delivery set 20, 30 is configured for engaging with an enteral feeding pump 40. The disposable fluid delivery set 20, 30 including a disposable tubing 21, 31 having a source end 21B, 31B for connection to a nutritional source and a patient end 21A, 31A for connection to a patient. The disposable tubing 21, 31 has a tubing wall and an area defined therein for the flow of fluid.

In one embodiment, the disposable tubing 21, 31 is a low grade tubing throughout its entire length. For example, the low grade tubing may be a low-grade PVC (polyvinyl chloride) tubing or other inexpensive tubing approved for use in the medical field. It should be noted that this invention is not limited to low-grade PVC tubing and that any tubing used in the medical field may be used, preferably inexpensive tubing. Low-grade PVC tubing is typically the standard tubing set used today in existing enteral feeding pump systems. The use of the low-grade PVC tubing set saves additional costs over using more expensive higher grade PVC tubing sets, especially tubing sets using silicone portions.

The compression portion 10 is configured to repeatably pump a large volume of medical fluids per stroke from a source end 21B, 31B to a patient end 21A, 31A. The compression portion 10 is durable and able to weather repeated compression over a longer period of time. The repeatable compression portion 10 of the fluid delivery set 20, 30 is helically coiled around a central C or vertical axis to define a cylindrical shape. Of course, other shapes are capable of displacing a large volume of fluid, such as coiled and spiral shapes. The compressing portion 10 includes at least two adjacent tubing walls joined or stacked around a central axis C for repeatable axial compression along the central axis C. The adjacent tubing walls are joined at wall contact points 12 where at least two adjacent tubing walls meet at a central portion of the adjacent tubing walls. In one embodiment, the adjacent tubing walls are joined at said wall contact points 12 using a solvent material to prevent distortion of the compression portion 10 during repeated compression.

The compression section 10 may have an adjustable number of coil turns. The number of coil turns, diameter of the tubing, and the diameter of the compression section is variable depending upon the desired volume of liquid stroked or displaced, the flow rate, type of tubing material, durometer of the tubing material, viscosity of the fluid, and other compression factors. For example, FIG. 1 illustrates a compression section 10 with seven coil turns. In another embodiment, the number of coil turns for the compression portion 10 may be seven with an inner diameter of 25 mm for the compression portion 10. In another example, the number of coil for the compression section 10 may be nine with an inner diameter of 0.916 inches for the compression portion 10. These are only examples and the number of coil turns and inner diameter may be adjusted according to desired characteristics discussed above.

Figure 2:
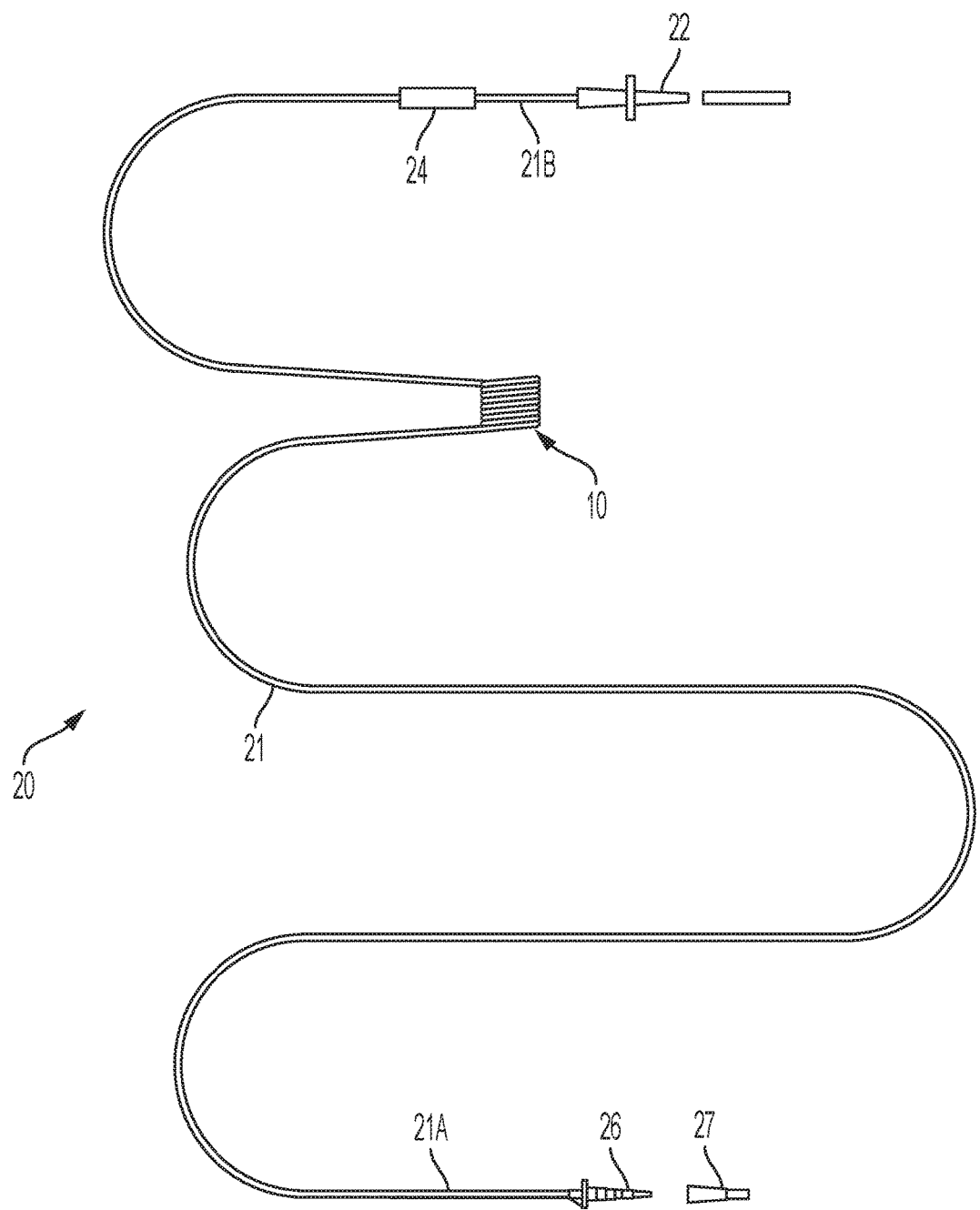
FIG. 2 is a plan view of a disposable fluid delivery set assembly (20) including a compression portion (10), a spike member (22) and a patient connector (26).
Figure 3:
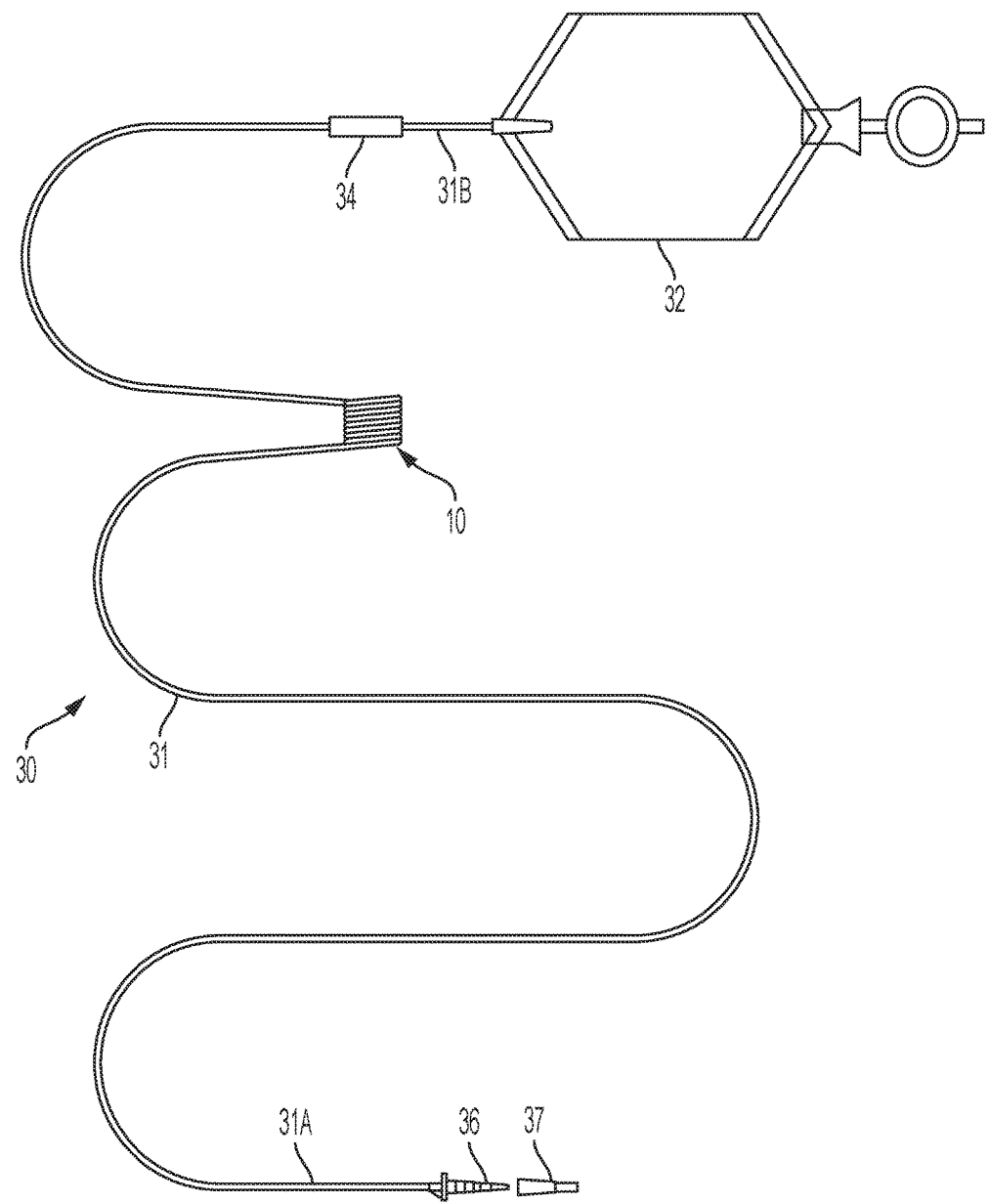
FIG. 3 is a plan view of a disposable fluid delivery set assembly (30), including a compression portion (10), a fluid fillable bag (32) and a patient connector (36).

Referring to FIGS. 2-3, the remainder of the fluid delivery set 20, 30 at each end of the compression section 10 is used to connect to the fluid source and the patient. The remainder of the disposable fluid delivery 20, 30 set may include a spike set 20, bag set 30, or other configurations. The spike set 20 may include a spike member 22 fluidly connected at the source end 21B of the tubing 21, one or more roller clamp members 24 positioned along the tubing 21, and a patient fitting 26 with a cap 27 fluidly connected at the patient end 21A. The bag set 30 may include a bag 32 fluidly connected at the source end 31B of the tubing 31, one or more roller clamp members 34 positioned along the tubing 31, a drip chamber (not shown) fluidly connected with the tubing 31 near the bag 32, and a patient fitting 36 with a cap 37 fluidly connected to the patient end 31A of the tubing 31. Other configurations or variations of the spike set 20 and bag set 30 may be used by adding or removing components to the fluid delivery sets 20, 30.

Figure 4:
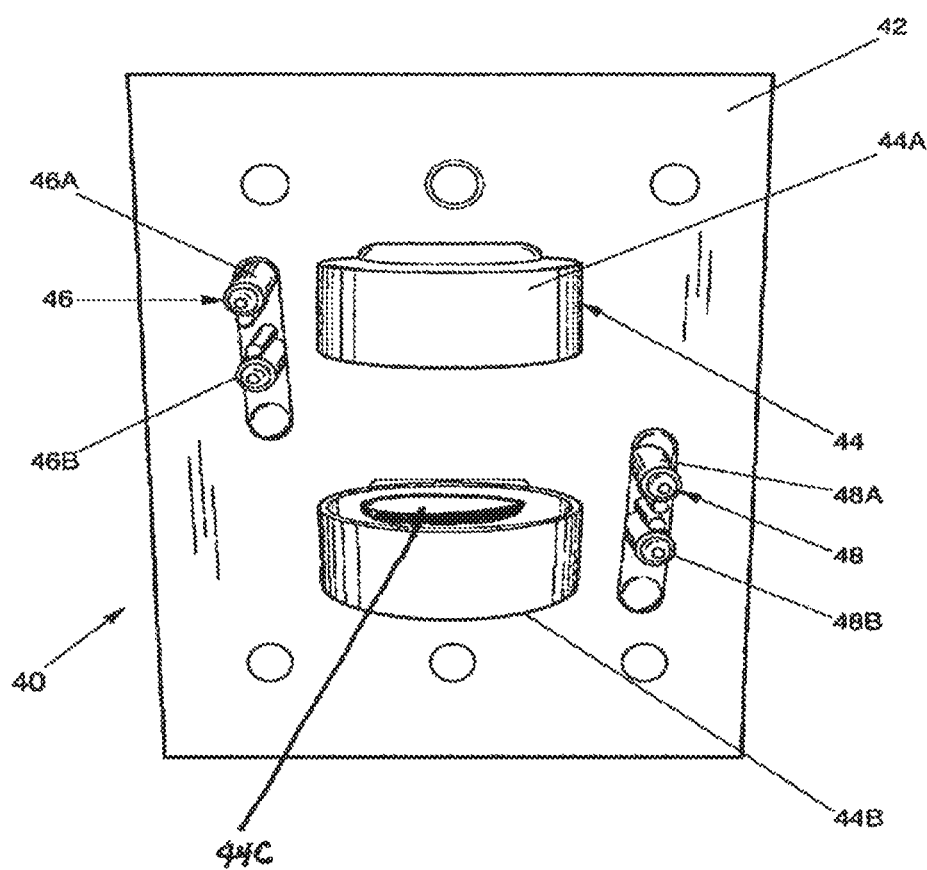
FIG. 4 is a front view of an enteral feeding pump mechanism for delivering medical fluids; including compression plates that cycle to compress and decompress the compression portion of either set of FIG. 2 or FIG. 3 (44A & 44B) and flow regulating pinch valves (46 & 48).
Figure 5:
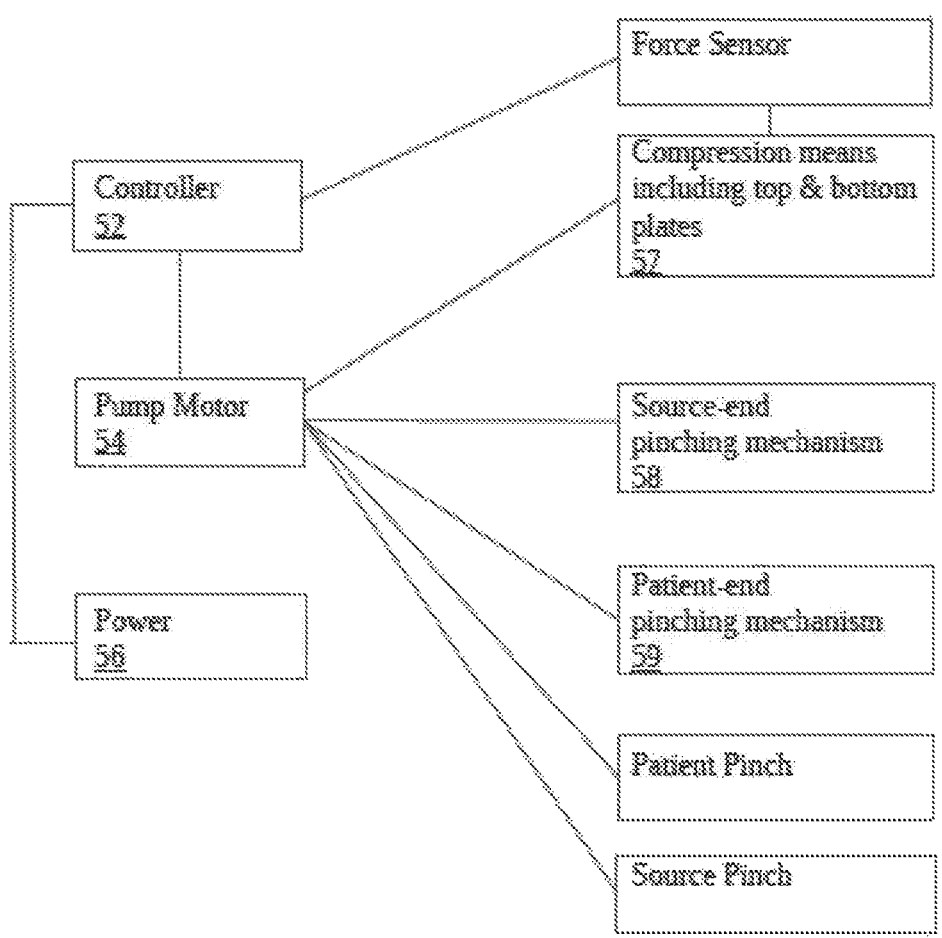
FIG. 5 is a block diagram of the operational components of the enteral feeding pump of FIG. 4.
Figure 6:
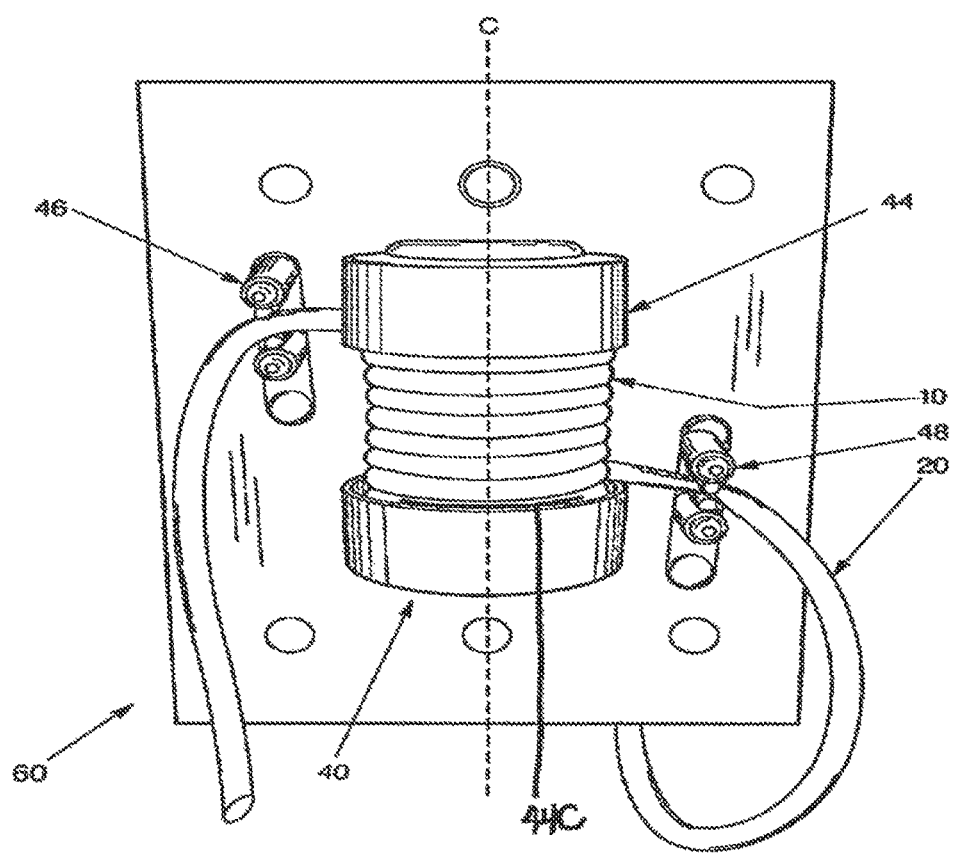
FIG. 6 is a front view of an enteral feeding pump system including an enteral feeding pump and disposable fluid delivery set including a compression portion (10) and force sensor (44C).

Referring to FIGS. 4-6, the enteral feeding pump 40 is configured to repeatedly and reliably compress the compression portion 10 of the fluid delivery set 20, 30 along a central axis C. The enteral feeding pump 40 including a housing 42, a pump motor unit 54 disposed within the housing 42, a controller 52 disposed within the housing 42 for directing the operation of the pump motor unit 54 to provide selective sequential compression, and a repeatable compression means for compressing the compression portion 10 of the fluid delivery set 20, 30.

In one embodiment, the repeatable compression means includes a plate system 44 driven by the pump motor unit 54 and disposed within the housing 42. The plate system 44 includes a top plate 44A respectively positioned to a bottom plate 44B. The top plate 44A and the bottom plate 44B configured to receive the compression portion 10 of a fluid delivery set 20, 30 with an interior portion of the top plate 44A and bottom plate 44B. The top plate 44A are operationally connected to the pump motor unit 54 to axially move the top plate 44A towards the bottom plate 44B.

The enteral feeding pump 40 may also include a regulation means for regulating the flow of medical fluid into and out of the compression portion 10 of the fluid delivery set 20, 30. In one embodiment, the means for regulating a flow of medical fluid are source end 46 and patient end 48 pinching mechanisms disposed within the housing 42 and operationally connected to the pump motor unit (not shown). The source end pinching mechanism 46 includes first source end 46A and second source end 46B pinching members. The first source end pinching member 46A respectively positioned to the second source end pinching member 46B. The first source end 46A and second source end pinching members 46B configured to receive a portion of a fluid delivery set 20, 30 between said source end 21B, 31B of the fluid delivery set 20, 30 and the compression portion 10 of the fluid delivery set 20, 30. The first source end pinching member 46A, second source end pinching member 46B, or both are operationally connected to the motor unit (not shown) to move the first source end pinching member 46A relatively towards said second source end pinching member 46B to squeeze or apply pressure to a portion of the fluid deliver set 20, 30 to regulate the flow of fluid through the fluid delivery set 20, 30 from a fluid source.

The patient end pinching mechanism 48 includes first patient end 48A and second patient end pinching members 48B. The first patient end pinching member 48A respectively positioned to the second patient end pinching member 48B. The first patient end 48A and second patient end pinching members 48B configured to receive a portion of the fluid delivery set 20, 30 between the patient end 21A, 31A of the fluid delivery set 20, 30 and the compression portion 10 of the fluid delivery set 10. The first patient end pinching member 48A, second patient end pinching member 48B, or both operationally connected to the pump motor unit 54 to move the first patient end pinching member 48A relatively towards the second patient pinching member 48B to squeeze or apply pressure to a portion of the fluid delivery set 20, 30, which regulates the flow of fluid through the fluid delivery set 20, 30 and to the patient.

When the pinching members 46A, 46B, 48A, 48B apply enough pressure when engaging a portion of the fluid delivery set 20, 30, the flow of liquid is "pinched off" to prevent the flow of fluid through either the patient end 21A, 31A, source end 21B, 31B, or both. This is called a closed position. When the pinching members 46A, 46B, 48A, 48B reduce or eliminate the pressure on the portion of the fluid delivery set 20, 30, the flow of liquid is allowed to return through either the patient end 21A, 31A, source end 21B, 31B, or both. This is called an open position.

Referring to FIG. 5, a block diagram 50 depicts the key components of the enteral feeding pump 40. A controller 52 is in electrical communication with the pump motor unit 54 to direct the selective sequential compression. The pump motor 54 is operationally connected with the plate system 57 and the pinching mechanisms 58, 59. Upon direction from the controller 52, the pump motor 54 drives the plate system 57, source end pinching mechanism 58, and patient end pinching mechanism 59 in selective sequential compression described further herein to provide unidirectional flow of liquid through a fluid delivery set 20, 30. The controller 52, pump motor 54, and power source 56 and methods of communication therebetween are known in the art.

In another embodiment, the means for regulating a flow of medical fluid into and out of the compression portion 10 of the fluid delivery set 20, 30 includes two or more valves 72, 74 fluidly connected at a patient end 21A, 31A and source end 21B, 31B of the fluid delivery set 20, 30. For example, a source end one-way valve 74 is fluidly connected between the source end 21B, 31B and the compression portion 10 of the fluid delivery set 20, 30. In addition, a patient end one-way valve 72 fluidly connected between the patient end 21A, 31A and the compression portion 10 of the fluid delivery set 20, 30. The valves 72, 74 are preferably one-way valves or other valves which in combination allow fluid to flow unidirectionally.

In one specific example, the source end one-way valve 74 may be implemented as a check valve that is fluidly connected between the source end 21B, 31B and the compression portion 10 of the fluid delivery set 20, 30. The patient end one-way valve 72 may be implemented as a check valve that is fluidly connected between the patient end 21A, 31A and the compression portion 10 of the fluid delivery set 20, 30. In general, a check valve a valve that closes to prevent backward flow of liquid. A check valve enables flow in one direction and automatically prevents back flow (reverse flow) when fluid in the line reverses direction. Check valves are one of the few self-automated valves that do not require assistance to open and close. Check valves are flow sensitive and rely on the line fluid to open and close. An internal disc enables flow to pass forward, which opens the valve. A disc begins closing the valve as forward flow decreases or is reversed, depending on the design. Construction is normally simple with only a few components such as the body, seat, disc, and cover. Depending on design, there may be other items such as a stem, hinge pin, disc arm, spring, ball, elastomers, and bearings.

Since the compression portion 10 must be installed so that it draws fluid from the source and delivers to the patient, utilizing check valves 72, 74 enables the coil to be installed into the pump in either orientation. When the pump is started, an initialization process determines the location of the fluid source.

In operation, the compression portion 10 is repeatably compressed without distortion along a central axis C by the enteral feeding pump 40 to flow fluid unidirectionally through the fluid delivery set 20, 30 using selective sequential compression. In the embodiment using the pinching mechanisms 46, 48, when the patient end pinching mechanism 48 is in an open position, the compression portion 10 is compressed or stroked into a compression position to allow the fluid to flow out of the compression portion 10 and through the patient end 21A, 31A. Next, the patient end pinching mechanism 48 is placed in a closed position and the source end pinching mechanism 46 is placed in an open position. The compression portion 10 then rebounds from the compressed position to draw fluid through the source end 21B, 31B and into the compression portion 10. The amount of rebound is a function of the tubing grade, quality and the degree of tubing compression characteristics. Note, this selective sequential compression may be adjusted using different predetermined timing sequences to increase or decrease the desired flow rate and volume of fluid delivered to the patient.

Another means to create directed flow is to use the patient end and source end pinching mechanisms 46, 48 in the remaining uncoiled tubing 21, 31 near both ends of the compressed portion 10. The two pinching mechanisms 46, 48 alternately open and close in concert, or selective sequential compression, with the compression portion cycles. The following sequence produces unidirectional flow: 0) patient pinch mechanism close 1) source pinch mechanism open 2) compressing portion release 3) source pinch mechanism close 4) compressing portion compress 5) patient pinch mechanism close 6) source pinch mechanism open 7) compressing portion release 8) source pinch mechanism close 9) patient pinch mechanism open, and so forth.

As described above, fluid flow may be also directed by the inclusion of one way valves 72, 74 (e.g., check valves) in the remaining uncoiled tubing 21, 31 near both ends of the compression portion 10. With a series of compressions and releases, fluid alternately forces one valve to open and another valve to close. The result is unidirectional flow. In operation, the compressing portion 10 moves along a central C or vertical axis for fluid to flow unidirectionally within the fluid delivery set 20, 30, when the compressing portion 30 is in a compressed position, the fluid is forced out of the fluid delivery set through a first valve 72 at the patient end, when the compressed portion 10 rebounds from the compressed position, fluid is drawn into the fluid delivery set through a second valve 74 at the source end.

Figure 7:
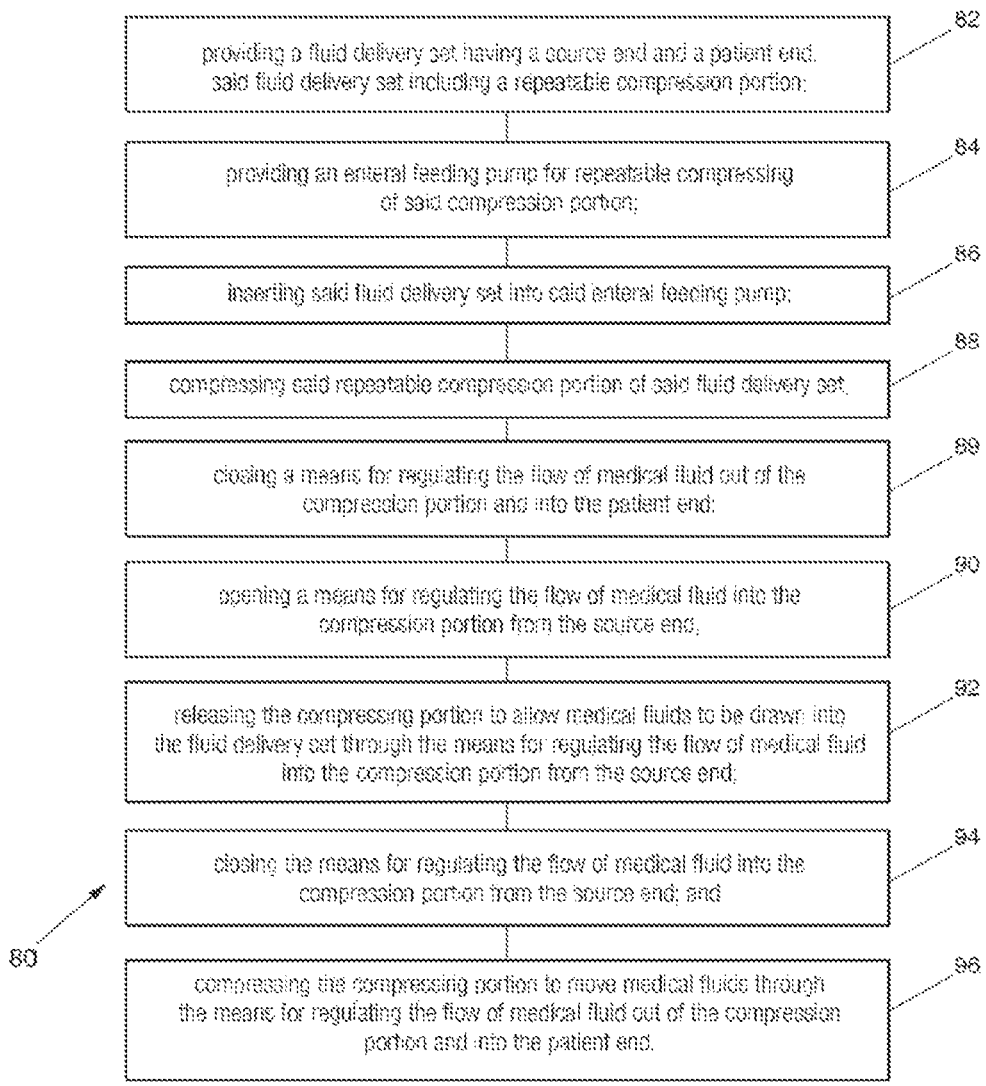
FIG. 7 is a flow diagram of a method for flowing fluid from source to patient using an enteral pumping system including an enteral feeding pump and disposable fluid delivery set having a compression portion.

In FIG. 7, the invention also includes a method for flowing fluid unidirectionally using an enteral pumping system including a disposable fluid delivery set and enteral feeding pump for delivery medical fluids 80. The method includes the following steps. First, a fluid delivery set is provided which includes a source end, a patient end, and the repeatable compression portion 82. Second, the enteral feeding pump is provided for repeatable compressing of the compression portion and regulating the flow of fluid into and out of the compression portion 84. Third, the fluid delivery set is inserted into the enteral feeding pump 86. In one embodiment, the fluid delivery set is color coded to mark the orientation of the compression portion within the enteral feeding pump. Fourth, the repeatable compression portion of the fluid delivery set is compressed using the enteral feeding pump 88. Fifth, a regulating means closes the flow of medical fluid out of the compression portion and into the patient end using the enteral feeding pump 89. Sixth, a regulating means opens the flow of medical fluid into the compression portion from the source end using the enteral feeding pump 90. Seventh, the compressed portion is released using the enteral feeding pump to allow medical fluids to be drawn into the fluid delivery set through the regulating means and into the compression portion from the source end 92. Eighth, the regulating means closes the flow of medical fluid into the compression portion from the source end using the enteral feeding pump 94. Ninth, the compressing portion is compressed by the enteral feeding pump to move medical fluids out of the compression portion, through the regulating means, and into the patient end 96. This process is continued depending upon the flow rate and volume of liquid desired for a patient.

In another embodiment, the invention also may provide a method for fluid flowing unidirectionally using the enteral feeding pump system. First, the method provides an enteral feeding pump system containing replaceable low-grade PVC tubing set having a source end and a patient end. The source end is connected to a fluid source and the patient end is connected to a patient. The compression portion of the PVC tubing set is configured in a coiled or cylindrical shape. The PVC tubing is coiled to provide at least two tubing walls of the PVC tubing stacked along a vertical axis. The tubing walls of the compressing portion are joined together by solvent welding. The compressing portion fluidly connected between the source end and the patient end. The first valve is connected to the patient end and a second valve connected to the source end. Second, the valve is closed at the patient end. Third, the valve is opened at the source end. Fourth, the compressing portion is released to allow fluid to be drawn into the tubing set through the second valve at the source end. Fifth, the valve at the source end is closed. Sixth, the compressing portion is compressed to move fluid out of the tubing set through the first valve at the patient end. Seventh, the valve is closed at the patient end. Eighth, the valve is opened at the source end. It has consistent geometry and the method of bonding adjacent turns results in minimum impact on the compression characteristics of the coil.

The present invention also includes a method of manufacture of a repeatable compression portion of a disposable fluid delivery set 100. The compression portion of a disposable fluid delivery set may be produced by the following steps for solvent welding. First, a disposable tubing is provided that is used for medical purposes 102. Second, the tubing is helically coiled around a central axis to define a cylindrical shape. Third, the tubing is tensioned and properly pitched during coiling to provide at least two adjacent tubing walls around the central axis for repeatable compression 104. In one embodiment, the tension on the tubing is provided by a weight of 250 gm and a pitch of 2.4 coils/cm. This is merely an example of the weight and pitch that can be used. Fourth, a dispensing solvent is applied at wall contact points where at least two adjacent tubing walls meet at a central portion of said adjacent tubing walls to join adjacent tubing walls during coiling 106. Fifth, the tubing is coiled under tension and joined by dispensing solvent to join adjacent tubing walls until desired number of coil turns is reached to define a cylindrical shape of the compression portion of the fluid delivery set 108. In an alternative embodiment, the solvent may be applied by dipping a compression portion in a solvent dipping bath to join the tubing walls together. The number of turns for the compression portion is variable depending upon the desire volume displaced upon a stroke.

The invention also includes a coiling apparatus 110 for producing a repeatable compression portion 10 of a disposable fluid delivery set 20, 30. The coiling apparatus includes a spinning mandrel 120 and a solvent dispenser 140. The mandrel 120 and solvent dispenser 140 having a power source, a motor unit for turning the mandrel, a controller for directing the operation of the motor unit and controller, and a solvent source. The mandrel is configured for helically coiling a disposable tubing under controlled tension to produce a compression portion 10 of the tubing defining a cylindrical shape. The mandrel 120 includes a retaining means 122 for the tubing on the mandrel during coiling. A solvent dispenser 140 is positioned near said mandrel 120 to contact the compression portion 10 of the tubing. The dispenser 140 is in fluid connection with a solvent source. The dispenser 140 provides a solvent to join wall contact points of adjacent tubing walls of the compression portion 10 during helical coiling of the tubing. The production of the compression portion 10 using the method and coiling apparatus 110 above result in a consistent coil diameter which is critical. The end result is compression portion which has coil turns bonded by the solvent weld effect. The main advantage of this is there is no additional material introduced that could distort the compression characteristics of the coil (as would occur if an adhesive were used).

The compression portion 10 is helically coiled around the central axis C. During engagement with the enteral feeding pump 40, the compression portion 10 is stroked or displaced along the central axis C. As shown generally in the FIGS. 1-7, the central axis C of the compression portion 10 is defined as a vertical axis or oriented at a 90 degree angle. However, it is contemplated that the central axis C of the compression portion 10 may be defined as a horizontal axis or oriented at an 180 degree angle or somewhere in between. To accommodate the stroking of the compression portion 10 at a 180 degree angle or along a horizontal axis, the enteral feeding pump 40 may have a plate system 44 which is oriented along a horizontal axis and the top and bottom plates 44A, 44B may include a retaining member or other means for seating the compression portion 10 within the top and bottom plates 44A, 44B.

In another embodiment, the disposable fluid delivery set assembly consists of a source end, a compression portion and a patient end connector with integral check valve. The integral check valve has a cracking pressure that is higher than the maximum elevation difference between the source container and the patient, which prevents excess flow. This configuration allows unidirectional pumping when the proximal tubing section relative to the compression portion is captured in a pinch valve.

To utilize the lower cost features of the above described sets, a pump with oscillating plate mechanisms as described in FIG. 6, has been developed. This pump consists of two plate mechanism assemblies with one plate from each mechanism connected to a common lever with central, motor actuated fulcrum. The pump also includes a single proximal pinch valve for each compressing plate pair. The pinch valves are activated and de-activated in a manner that causes medical fluid to flow through either compression portion of two sets. This allows programmed pumping of two different fluids into patient. Independent pumping is achieved when the pinch valve of the de-selected source is in the closed position. After one or two strokes of the pumping plates, a vacuum is created in the compression portion of the de-activated set. This physically frees the coil from the oscillating plates, thus stopping flow. Operation of the pinch valve of the second set continues to cycle normally resulting in flow from the selected source. Switching of the pinch valve functioning changes the pumping source.

In view of the foregoing, a new and novel enteral feeding pump system 60, 70 is provided which provides compression using a low cost tubing set for unidirectional flow of fluid. The enteral feeding pump system 60, 70 meets flow demand while not stressing other mechanical components. Also, the enteral pumping system has low grade tubing, which costs less than high grade PVC tubing, and does not contain associated hardware that adds cost to an enteral pumping system.

The method of operation of the enteral feeding pump system incorporating the capture mechanism 200 may operate in accordance with the following steps but is merely an example and other methodologies of operation discussed above may be used. First, a fluid delivery set is provided having a source end and a patient end. Second, an enteral feeding pump is provided for regulating the flow of fluid into and out of the fluid delivery set. Third, a tube section of the tubing set made of low-grade PVC tubing is inserted within a capture mechanism operationally connected to an enteral feeding pump. Fourth, the tube section is reeled within the capture mechanism around a central axis to provide a helically coiled repeatable compression section of the tubing set within the capture mechanism. The repeatable compression portion of said fluid delivery set is compressed using the enteral feeding pump. A means for regulating the flow of medical fluid out of the compression portion and into the patient end using the enteral feeding pump is closed. A means for regulating the flow of medical fluid into the compression portion from the source end using the enteral feeding pump is opened. The compressing portion is released using the enteral feeding pump to allow medical fluids to be drawn into the fluid delivery set through the means for regulating the flow of medical fluid into the compression portion from the source end. The means for regulating the flow of medical fluid into the compression portion from the source end using the enteral feeding pump is closed. Next, the compressing portion is compressed using the enteral feeding pump to move medical fluids through the means for regulating the flow of medical fluid out of the compression portion and into the patient end.

Figure 8:
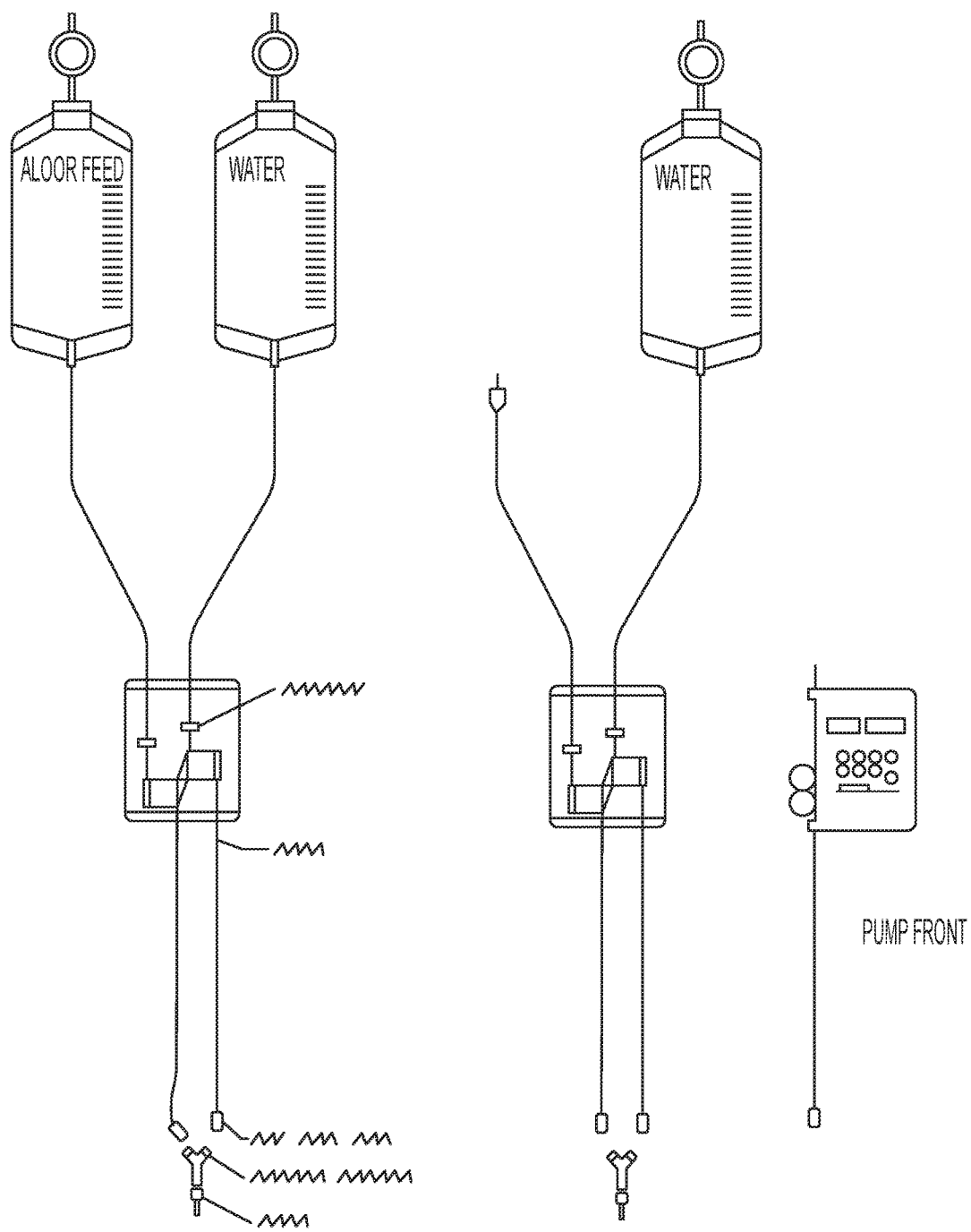
FIG. 8 a schematic diagram of the two set pump with set assembly features.

FIG. 8 illustrates a schematic diagram of the two set pump with set assembly features.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for flowing fluid comprising:
providing a fluid delivery set having a source end and a patient end with a repeatable compression portion intermediate the ends, the fluid delivery set comprising a disposable tubing set made of low-grade PVC tubing throughout its length;
providing an enteral feeding pump for regulating the flow of fluid into and out of the fluid delivery set;
compressing said repeatable compression portion made of low-grade PVC tubing of said fluid delivery set using the enteral feeding pump;
selectively closing a first means for regulating the flow of medical fluid out of the compression portion; and
selectively opening a second means upstream of the repeatable compression portion for regulating the flow of medical fluid into the compression portion from the source end, the first means and the second means comprising check valves positioned at opposite ends of the disposable tubing set.

2. A disposable fluid delivery set assembly comprises:
a source end;
a compression portion; and
a patient end connector with an integral check valve, the integral check valve having a cracking pressure that is higher than a maximum elevation difference between a source container and a patient, preventing excess flow and enabling unidirectional pumping when a proximal tubing section relative to the compression portion is captured in a pinch valve.

3. A method for flowing fluid unidirectionally using an enteral pumping system including a disposable fluid delivery set and enteral feeding pump for delivery medical fluids comprises:
providing a fluid delivery set which includes a source end, a patient end, and the repeatable compression portion;
providing the enteral feeding pump is for repeatable compressing of the compression portion and regulating the flow of fluid into and out of the compression portion;
inserting the fluid delivery set into the enteral feeding pump;
compressing the repeatable compression portion of the fluid delivery set using the enteral feeding pump;
closing the flow of medical fluid out of the compression portion with a regulating means and into the patient end using the enteral feeding pump;
opening the regulating means opens to cause the flow of medical fluid into the compression portion from the source end using the enteral feeding pump;
releasing the compressed portion using the enteral feeding pump to allow medical fluids to be drawn into the fluid delivery set through the regulating means and into the compression portion from the source end;
closing the regulating means to close the flow of medical fluid into the compression portion from the source end using the enteral feeding pump; and
compressing the compressing portion by the enteral feeding pump to move medical fluids out of the compression portion, through the regulating means, and into the patient end.

4. The method of claim 3 wherein the regulating means is a check valve.

* * * * *